(12) United States Patent
Kratzberg et al.

(10) Patent No.: US 11,980,540 B2
(45) Date of Patent: May 14, 2024

(54) SIDE BRANCH AORTIC REPAIR GRAFT WITH WIRE LUMEN

(71) Applicant: Cook Medical Technologies LLC, Bloomington, IN (US)

(72) Inventors: Jarin A. Kratzberg, West Lafayette, IN (US); Erik E. Rasmussen, Slagelse (DK); Ruwan Sumanasinghe, Carmel, IN (US); Woong Kim, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 678 days.

(21) Appl. No.: 17/117,691

(22) Filed: Dec. 10, 2020

(65) Prior Publication Data
US 2021/0093436 A1 Apr. 1, 2021

Related U.S. Application Data

(63) Continuation of application No. 15/591,868, filed on May 10, 2017, now Pat. No. 10,869,747.

(51) Int. Cl.
*A61F 2/06* (2013.01)
*A61F 2/07* (2013.01)

(52) U.S. Cl.
CPC ............... *A61F 2/06* (2013.01); *A61F 2/064* (2013.01); *A61F 2/07* (2013.01); *A61F 2220/005* (2013.01); *A61F 2220/0075* (2013.01)

(58) Field of Classification Search
CPC .... A61F 2/06; A61F 2/07; A61F 2/064; A61F 2220/005; A61F 2220/0075; A61F 2002/065
See application file for complete search history.

(56) References Cited

U.S. PATENT DOCUMENTS

| 4,313,231 A | 2/1982 | Koyamada |
| 5,123,917 A | 6/1992 | Lee |
| 5,411,550 A | 5/1995 | Herweck et al. |
| 5,593,417 A | 1/1997 | Rhodes |
| 5,632,772 A | 5/1997 | Alcime et al. |
| 5,667,523 A | 9/1997 | Bynon et al. |
| 5,681,345 A | 10/1997 | Euteneuer |
| 6,214,039 B1 | 4/2001 | Banas et al. |
| 6,398,803 B1 | 6/2002 | Layne et al. |
| 6,451,050 B1 | 9/2002 | Rudakov et al. |
| 6,916,335 B2 | 7/2005 | Kanji |
| 7,105,017 B2 | 9/2006 | Kerr |
| 7,678,271 B2 | 3/2010 | Chobotov et al. |
| 8,252,036 B2 | 8/2012 | Cartledge et al. |

(Continued)

FOREIGN PATENT DOCUMENTS

GB 2 269 104 A 2/1994
WO WO 2008/007048 A1 1/2008

*Primary Examiner* — Tuan V Nguyen
(74) *Attorney, Agent, or Firm* — Crowell & Moring LLP

(57) ABSTRACT

An endoluminal graft includes a tubular graft material having a closed sleeve integral with the tubular graft material. The closed sleeve extends a distance along the tubular graft material. A length of wire extends at least partially along the distance and is enclosed by the sleeve. The tubular graft material and the sleeve may comprise a single piece of graft material. The sleeve may be a closed circumferential sleeve and/or a closed longitudinal sleeve.

20 Claims, 9 Drawing Sheets

(56) References Cited

U.S. PATENT DOCUMENTS

| | | | |
|---|---|---|---|
| 8,574,288 B2 * | 11/2013 | Hartley | A61F 2/07 623/1.35 |
| 8,591,782 B2 | 11/2013 | Nakayama et al. | |
| 10,364,518 B2 * | 7/2019 | Van Hulle | D03D 11/02 |
| 2002/0029077 A1 | 3/2002 | Leopoid et al. | |
| 2002/0099436 A1 | 7/2002 | Thornton et al. | |
| 2003/0135269 A1 | 7/2003 | Swanstrom | |
| 2004/0243221 A1 | 12/2004 | Fawzi et al. | |
| 2005/0102022 A1 | 5/2005 | Solovay et al. | |
| 2007/0219622 A1 | 9/2007 | Kuppurathanam | |
| 2010/0228335 A1 | 9/2010 | Schorgl et al. | |
| 2011/0166638 A1 | 7/2011 | Bebb et al. | |
| 2012/0123327 A1 | 5/2012 | Miller | |
| 2014/0120287 A1 | 5/2014 | Jacoby et al. | |
| 2014/0121761 A1 | 5/2014 | McDonald et al. | |
| 2015/0005869 A1 | 1/2015 | Soletti et al. | |

* cited by examiner

FIG. 12D     FIG. 12E

SIDE BRANCH AORTIC REPAIR GRAFT WITH WIRE LUMEN

RELATED APPLICATION

This application is a continuation of U.S. application Ser. No. 15/591,868, filed on May 10, 2017, pending, which is incorporated herein by reference.

TECHNICAL FIELD

The present disclosure relates to an endovascular repair graft, and in particular, to a side branch aortic repair graft for treating conditions such as an aortic aneurysm.

BACKGROUND

Manufacturers of aortic repair grafts invest a significant amount of resources in overcoming challenges associated with non-typical cases of aortic disease, where off-the-shelf devices are not suitable due to the complex geometries of diseased areas of the aorta. In such cases, physicians may initiate a request for the manufacture of a customized device, where a three-dimensional computed tomography (3dCT) is performed on the patient, and the imaging data is used to custom design and build a patient-specific device.

However, a personalized aortic device requires significant time to manufacture, in some cases, exceeding six days. Currently, a significant portion of the manufacture time for a personalized aortic device is associated with hand-stitching nitinol rings and wires into graft material of a length specific to a patient's anatomy, for example, in the manufacture of repair grafts for side branches of aortic vessels. The time required to hand stitch one nitinol support ring to a side branch graft may exceed 30 minutes, as the total number of hand stitched knots for a support ring may exceed 50, depending on the diameter of the graft. Likewise, the time required to hand stich a wire spine to a length of a side branch graft may exceed 3 minutes, as the total number of hand stitched knots for a spine may exceed 10, depending on the length of the branch. For a personalized aortic device with four side branches, the time required for hand stitching may exceed a half day of labor.

As timing for treatment of an aneurysm may be critical to a patient's well-being, a shorter turnaround time could benefit the patient, and also alleviate complications of the aortic disease during the manufacture of a patient-specific aortic device, such as for example, rupture of an aortic aneurysm. Reduction in fabrication complexities and time will also reduce manufacturing costs. In this regard, there is a need for a more simple, quicker manufacture of personalized aortic devices, and an improved design for aortic repair grafts useable in personalized aortic devices.

BRIEF SUMMARY

In one aspect, an endoluminal graft includes a tubular graft material having a closed sleeve integral with the tubular graft material, the closed sleeve extending a distance along the tubular graft material, and a length of wire extending at least partially along the distance and enclosed by the sleeve. The tubular graft material and the sleeve may comprise a single piece of graft material.

The sleeve may be a closed circumferential sleeve. The closed circumferential sleeve may be positioned at an end of the endoluminal graft. The length of wire enclosed by the sleeve may be formed into a generally closed shape. The sleeve may also be a closed longitudinal sleeve or a closed helical sleeve. Alternatively, the sleeve may extend a longitudinal distance, a circumferential distance, and/or a combination thereof.

A second closed sleeve may be integral with the tubular graft material. The second closed sleeve may extend a second distance along the tubular graft material. A second length of wire may extend at least partially along the second distance and be enclosed by the second sleeve.

In another aspect, an endoluminal graft includes a tubular graft material having a closed sleeve positioned at an end of the endoluminal graft and extending about a circumference of the end, and a wire having a length formed into a generally closed shape, wherein the length of the wire formed into the generally closed shape is at least partially enclosed within the closed sleeve. The closed sleeve may be integral with the tubular graft material, characterized by the absence of a circumferential seam. The tubular graft material and the closed sleeve may comprise a single piece of woven graft material.

The closed sleeve may include an end length of the graft material folded outward onto an exterior of the graft material. Alternatively, the closed sleeve may include an end length of the graft material folded inward onto an interior of the graft material. The closed sleeve may include a continuous seam securing an end of the graft material to the graft material. The wire may extend through an opening in the sleeve.

In another aspect, an endoluminal graft includes a tubular graft material having a length and a circumference, a closed circumferential sleeve extending about the circumference at an end of the length, a closed longitudinal sleeve extending along the length, and a wire positioned at least partially within the closed circumferential sleeve and the closed longitudinal sleeve.

The wire may include a first length formed into a generally closed shape positioned at least partially within the closed circumferential sleeve, and a second length formed into a spine positioned at least partially within the closed longitudinal sleeve. The endoluminal graft may also include an opening in the closed circumferential sleeve and an opening in the closed longitudinal sleeve through which the wire extends.

The closed circumferential sleeve and the closed longitudinal sleeve may comprise a single piece of graft material. The circumferential sleeve and the longitudinal sleeve may be integral with the tubular graft material.

In another aspect, an endoluminal graft incudes a tubular graft material having a closed sleeve positioned at an end of the endoluminal graft and extending about a circumference of the end. A wire has a length formed into a generally closed shape, and an opening in the sleeve is configured to receive the wire. The wire extends through the opening such that the length of the wire formed into the generally closed shape is at least partially enclosed within the closed sleeve.

The closed sleeve may include an end length of the graft material folded outward onto an exterior of the graft material. The closed sleeve may also include an end length of the graft material folded inward onto an interior of the graft material.

The closed sleeve may include a continuous seam securing an end of the graft material to the graft material. The seam may include a single string forming a plurality of stitches. The seam may include a thermoplastic weld. The seam may include an adhesive.

The closed sleeve may be integral with the tubular graft material. The closed sleeve may be characterized by the absence of a seam.

An end of the length of wire formed into the generally closed shape may terminate within the closed sleeve. An end of the length of wire formed into the generally closed shape may terminate in a loop.

The closed sleeve may extend about an entirety of the circumference of the end of the endoluminal graft. The closed sleeve may extend about a portion of the circumference of the end of the endoluminal graft.

The endoluminal graft may be characterized by the absence of a suture knot securing the length of the wire positioned within the sleeve to the graft material.

The wire may also include a spine extending from the length formed into the generally closed shape toward a second end of the endoluminal graft.

In another aspect, a method of making an endoluminal graft includes forming a closed sleeve at an end of the graft and extending about a circumference of the end, and advancing a length of wire formed into a generally closed shape through the closed sleeve. The method may also include creating an opening in the closed sleeve, and advancing the length of wire formed into the generally close shape into the closed sleeve through the opening. The closed sleeve may be integrally formed with the graft.

Creating the opening may include longitudinally cutting the end length of the tubular graft material. Forming the closed sleeve may include folding an end length of a tubular graft material onto the graft material. Forming the closed sleeve may also include securing an end of the graft material to the graft material. Securing the end of the graft material to the graft material may include forming a continuous seam. Securing the end of the graft material to the graft material may include machine sewing a continuous seam.

In another aspect, an endoluminal graft includes a tubular graft material having a closed sleeve positioned at an end of the endoluminal graft and extending about a circumference of the end, the closed sleeve being integral with the tubular graft material. A wire has a first length formed into a generally closed shape and a second length formed into a spine extending longitudinally along a length of the tubular graft material. The sleeve has an opening, and the wire extends through opening such that the length of the wire formed into the generally closed shape is at least partially enclosed within the closed sleeve. The closed sleeve may be integral with the tubular graft material.

In another aspect, an endoluminal graft includes a tubular graft material having a lumen extending a length of the graft material and a closed longitudinal sleeve extending along the length. The closed longitudinal sleeve has an opening at an end of the sleeve. A wire has a length formed into a spine extending along the length of the graft material. The spine extends through the opening and is at least partially enclosed within the closed longitudinal sleeve. The lumen and the closed longitudinal sleeve may comprise a single piece of graft material.

The closed longitudinal sleeve may include a portion of the graft material secured to the graft material. The closed longitudinal sleeve may include a continuous seam securing the portion of the graft material to the graft material. The seam may include a single string forming a plurality of stitches. The seam may include a thermoplastic weld. The seam may include an adhesive.

The closed longitudinal sleeve may be integral with the tubular graft material. The closed longitudinal sleeve may be characterized by the absence of a seam.

The closed longitudinal sleeve may extend along an entire length of the graft material. The closed longitudinal sleeve may extend along a portion of the length of the graft material.

The wire may further include a length formed into a generally closed shape and secured to an end of the graft material. The endoluminal graft may be characterized by the absence of a suture knot securing the spine enclosed within the closed longitudinal sleeve to the graft material.

In another aspect, a method of making an endoluminal graft includes forming a closed longitudinal sleeve along a length of tubular graft material, forming an opening into the closed longitudinal sleeve at an end of the sleeve, and advancing at least a portion of a length of wire formed into a spine through the opening and through the sleeve. The closed sleeve may be integrally formed with the tubular graft material.

Forming the longitudinal sleeve may include folding a portion of the graft material onto the graft material. Forming the longitudinal sleeve may include securing a portion of the graft material to the graft material. Securing the portion of the graft material to the graft material may include forming a continuous seam. Securing the portion of the graft material to the graft material may include machine sewing a continuous seam.

In another aspect, an endoluminal graft includes a tubular graft material having a lumen extending a length of the graft, a closed circumferential sleeve positioned at an end of the endoluminal graft and extending about a circumference of the end, and a closed longitudinal sleeve extending along the length of the graft. A wire is positioned at least partially within the closed circumferential sleeve and the closed longitudinal sleeve.

The wire may include a first length formed into a generally closed shape positioned at least partially within the closed circumferential sleeve, and a second length formed into a spine positioned at least partially within the closed longitudinal sleeve. The wire may extend through an opening in the closed circumferential sleeve and an opening in the closed longitudinal sleeve. The lumen, the closed circumferential sleeve, and the closed longitudinal sleeve may comprise a single piece of graft material. The circumferential sleeve and the longitudinal sleeve may be integral with the tubular graft material.

DETAILED DESCRIPTION

Described herein is an endovascular repair graft, for example, a side branch aortic repair graft with a wire lumen, that may be customized and efficiently manufactured according to a patient's unique anatomy. In particular, the endovascular repair graft significantly reduces and/or eliminates the hand stitching required to secure graft material to nitinol rings and wires for forming a lumen, improving manufacturing costs, efficiency, and overall design.

FIGS. 1A-1K are side views illustrating various endovascular repair grafts 800A-K according to an embodiment of the present disclosure, manufactured according to conventional weaving, knitting, or braiding processes, or a combination thereof. As described in detail below, the endovascular repair grafts 800A-K include a tubular graft material having a closed sleeve integral with the tubular graft material. The closed sleeve extends a distance along the tubular graft material, and a length of wire enclosed by the sleeve extends at least partially along the distance. The sleeve may be a closed circumferential sleeve, a closed longitudinal sleeve, or may include a combination of circumferential and longitudinal portions.

Figure 2:
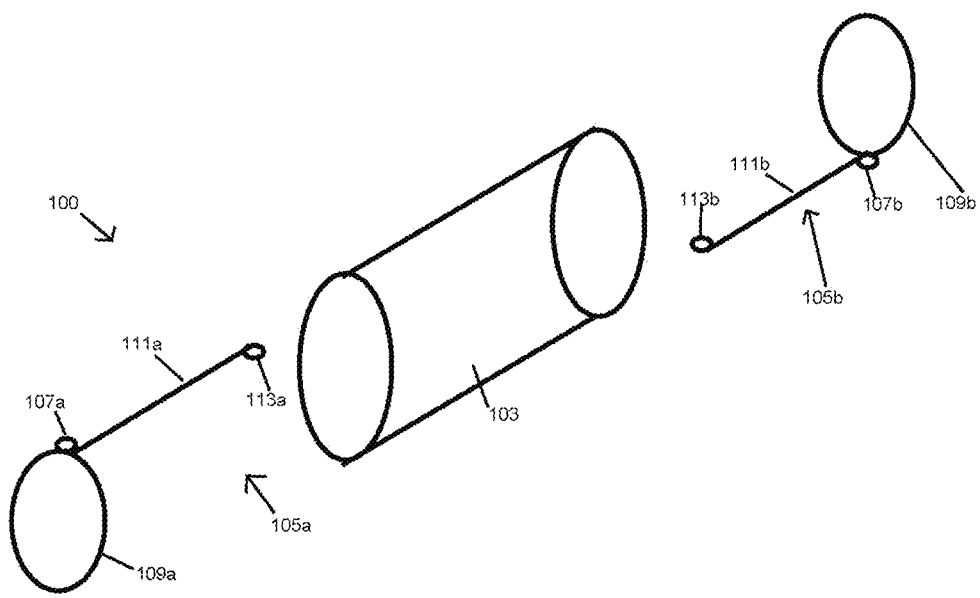
FIG. 2 is an exploded perspective view illustrating the components of an endovascular repair graft with a wire lumen.

FIG. 2 is an exploded perspective view illustrating the components of a side branch aortic repair graft 100. In general, the side branch aortic repair graft 100 of a personalized aortic device may include a length of tubular graft material 103, a first wire 105a and a second wire 105b.

The tubular graft material 103 may be comprised of any suitable graft material known in the art, including, for example, a polyester, such as Dacron. The length and diameter of the tubular graft material 103 may be selected according to the intended aortic vessel and a patient's unique anatomy.

The first wire 105a and the second wire 105b may be comprised of any suitable flexible wire or memory metal, including, for example, nitinol. The wires 105a and 105b may have varying thickness, for example, 0.006" to 0.008". As with the graft material 103, the overall length of the first wire 105a and the second wire 105b may be selected according to the intended aortic vessel and a patient's unique anatomy.

As shown in FIG. 2, the wires 105a and 105b may each comprise a length of wire formed into a "tad-pole" shape. That is, a first end of the wire 105a may be formed into a first small loop 107a or "pig-tail" shape, followed by a larger ring 109a, oriented approximately 90° relative to the small loop 107a, followed by a spine 111a, followed by a second small loop 113a or "pig-tail" shape. It should be appreciated that the ring 109a is not continuous, since the wire 105a is also used to form the small loop 107a and the spine 111a. The ring 109a may have a diameter selected according to the intended aortic vessel and a patient's unique anatomy. For example, the ring may have a diameter of 6 mm to 12 mm. Likewise, the length of the spine 111a may be selected according to a patient's unique anatomy. For example, the spine may be 20 mm to 25 mm. Although the ring 109a is shown as being generally circular, it should be appreciated that the ring 109a could have any other number of generally closed shapes, including for example, an oval shape (0), a D shape (D), or a square shape (□), to accommodate a patient's unique anatomy. The second wire 105b may have the same size and shape as the first wire 105a, including a first small loop 107b, a larger ring 109b, a spine 111b, and a second small loop 113b.

The first small loops 107a and 107b, and the second small loops 113a and 113b, are formed to encircle the ends of the wire 105a and 105b, thereby preventing puncture of the graft material 103 and/or the surrounding vessel once the repair graft 100 is deployed in a body. The first small loops 107a and 107b, and the second small loops 113a and 113b, also may act as an anchor to keep the position of the rings 109a and 109b, and the spines 111a and 111b, fixed relative to the graft material 103 (e.g., via suture knot), after the wires 105a and 105b have been inserted within and secured to the graft material 103, as discussed herein.

After the wires 105a and 105b have been secured to the graft material 103, the wires 105a and 105b operate to stent open the graft material 103, forming a lumen therethrough. In general, the wire rings 109a and 109b provide radial support for the graft material 103, while the spines 111a and 111b provide columnar support for the graft material 103. The first small loops 107a and 107b, the second small loops 113a and 113b, and the rings 109a and 109b, may also serve as structure for connecting the aortic repair graft 100 to one or additional main or branch repair grafts.

Figure 2A:
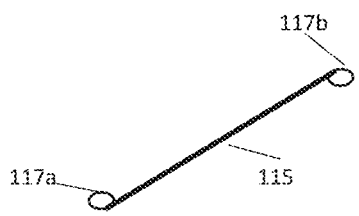
FIGS. 2A-C are perspective views of additional wire rings and wire spines useable with the endovascular repair grafts of the present disclosure.
Figure 2B:
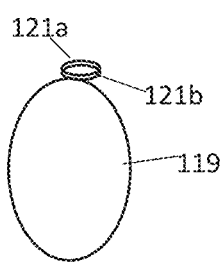
Figure 2C:
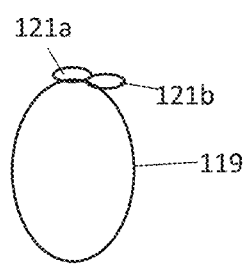

FIGS. 2A-C are perspective views of additional wire rings and wire spines useable with the endovascular repair grafts of the present disclosure. The wire spine 115 of FIG. 2A may be inserted into the longitudinal sleeves or pockets in the various embodiments described herein. Unlike the wire 105a and 105b, the wire spine 115 does not include not include a large ring 109a or 109b at one end. Instead, small loops 117a and 117b are formed to encircle the ends of the wire 105a and 105b, thereby preventing puncture of the graft material and/or the surrounding vessel once the repair graft is deployed in a body. The small loops 117a and 117b also may act as an anchor to keep the position of the spine 115 fixed relative to the graft material (e.g., via suture knot), after the spine 115 has been inserted within and secured to the graft material, as discussed herein.

The wire ring 119 of FIGS. 2B-C may be inserted into the circumferential sleeves or pockets in the various embodiments described herein. Unlike the wire 105a and 105b, the wire ring 119 does not include a spine 111a and 111b extending therefrom. Instead, small loops 121a and 121b are formed to encircle the ends of the wire ring 119, thereby preventing puncture of the graft material and/or the surrounding vessel once the repair graft is deployed in a body.

The wire ring 119 may be formed into any generally closed shape, as discussed above. The small loops 121a and 121b may be formed such that they overlap one another, as shown in FIG. 2B, or are adjacent to one another, as shown in FIG. 2C. The small loops 121a and 121b also may act as an anchor to keep the position of the wire ring 119 fixed relative to the graft material (e.g., via suture knot), after the wire ring 119 has been inserted within and secured to the graft material, as discussed herein.

Figure 3:
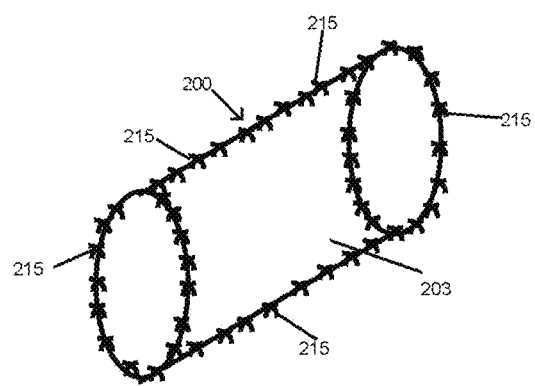
FIG. 3 is a perspective view illustrating a side branch aortic repair graft manufactured according to current practice, with graft material hand stitched to wires for forming a lumen.

FIG. 3 is a perspective view illustrating a repair graft 200 according to current practice, manufactured with graft material 203 hand stitched to wires forming a lumen therethrough. The aortic repair graft 200 generally includes a first wire and a second wire (not shown) in a "tad-pole" shape, as discussed above, inserted within the graft material 203. The first wire 105a and the second wire 105b are generally positioned within the graft material 203 such that the spine 111a of the first wire 105a and the spine 111b of the second wire 105b are positioned 180° or opposite one another, as illustrated in FIG. 2. Once the first wire 105a and the second wire 105b are positioned in the graft material 203, the graft material 203 may be secured to the rings 109a and 109b. Suture strings, such as polyester suture strings, are used to hand stich the graft material 203 to the first wire 105a and the second wire 105b via knots 215. As shown in the illustration of FIG. 3, a large number of knots 215 are required to properly and adequately secure the entire length of the first wire 105a and the second wire 105b to the graft material 203, including the first small loop, the ring, the spine, and the second small loop. As noted above, a significant portion of the manufacture time for a personalized aortic device is associated with this process. Similar repair grafts are shown and described in U.S. Pat. No. 8,574,288, the entirety of which is herein incorporated by reference.

Figure 4:
FIG. 4 is a top view of tubular graft material illustrating longitudinal cuts in the graft material for manufacturing an endovascular repair graft according to an embodiment of the present disclosure.
Figure 5:
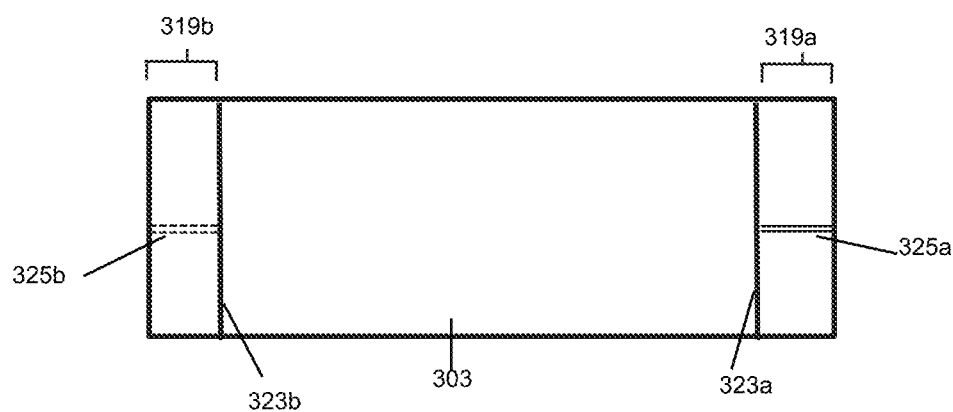
FIG. 5 is a top view of the tubular graft material of FIG. 4, with an end length thereof folded on and sewn to the graft material.

FIGS. 4-7 illustrate a repair graft 300 according to an embodiment of the present disclosure. FIG. 4 is a top view of a tubular graft material 303 illustrating a first longitudinal cut 317a and a second longitudinal cut 317b in the graft material 303 for manufacturing a repair graft according to the present disclosure. The first cut 317a and the second cut 317b may be made in the graft material 303 using any suitable means, including for example, a thermal knife, a soldering iron, or a blade. As shown in FIGS. 4 and 5, the cuts 317a (in the foreground) and 317b (in the background) may be made in the graft material 303 approximately 180° or opposite one another. The length of the first cut 317a and the second cut 317 may be selected to accommodate the size and shape of the small loop and larger ring of the first wire 105a and the second wire 105b. For example, a cut of approximately 2.5 mm may accommodate a generally circular ring formed in a wire having a thickness of 0.006" to 0.008".

As shown in FIG. 5, after the first cut 317a and the second cut 317b is complete, a first end length 319a and a second end length 319b of the graft material 303, having the length of the first cut 317a and the second cut 317b, may be folded radially outward to wrap around the tubular graft material 303, thereby forming cuffs around the graft material 303. Alternatively, the first end length 319a and the second end length 319b may be folded radially inward. After forming the cuffs, a first end 321a and a second end 321b of the graft material 303 may be secured to the graft material 303 along a first seam 323a and a second seam 323b. The first seam 323a and the second seam 323b may be formed by any suitable non-labor intensive means, including for example, suture string sewn with a conventional sewing machine, heat staking, or adhesives. While non-labor intensive means are preferred, it should be appreciated that labor intensive means may also be utilized, including hand-stitched knots using suture string.

Figure 6A:
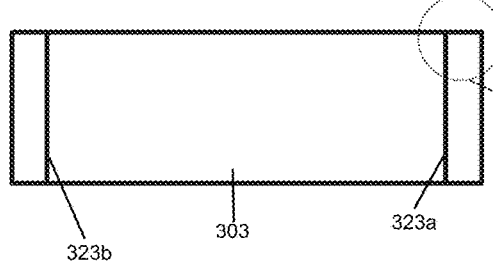
FIGS. 6A and 6B are side and partial cross-sectional views, respectively, illustrating a sleeve formed in the graft material of FIG. 5.
Figure 6B:
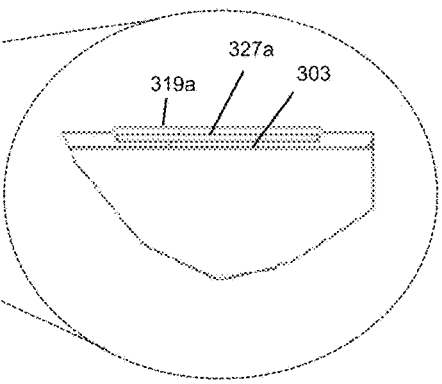

After the first end 321a and the second end 321b are secured to the graft material 303, a first slit 325a and a second slit 325b remain at the location of the first cut 317a and the second cut 317b, respectively. As shown in FIGS. 6A-B, a first annular sleeve 327a or pocket is formed between the first end length 319a and the graft material 303. Likewise, at the other end of the graft material 303, a second annular sleeve 327b (not shown) is formed between the second end length 319b and the graft material 303.

After the first annular sleeve 327a and the second annular sleeve 327b are formed, the first wire 105a and the second wire 105b may be "sleeved" into the first sleeve 327a and the second sleeve 327b. That is, the small loop 107a of the first wire 105a may be inserted through the first slit 325a into the first sleeve 327a. The larger ring 109a may then be fed into the sleeve 327a and rotated about the graft material 303 to "sleeve" or advance the ring 109a through the annular sleeve 327a, until the spine 111a and the second small loop 113a are the only lengths of the first wire 105a remaining outside of the sleeve 327a.

Once the small loop 107a and the larger ring 109a are fully sleeved into the sleeve 327a, the spine 111a may be secured to the graft material 303, for example, with hand stitched suture knots 315. A hand stitched suture knot 315 may also be used to secure the first small loop 107a and the second small loop 113a to the graft material 303. The sleeve 127a effectively secures the graft material 303 to the larger ring 109a, such that no hand-stitched suture knots 315 are required to secure the larger ring 109a to the graft material 303. However, it should be appreciated that one or more hand stitched suture knots 315 may be used to further secure the larger ring 109a to the graft material 303. The second wire 105b may be secured to the graft material 303 in a similar manner. Alternatively, the spine 115 and the wire ring 119 of FIGS. 2A-C may be used.

Figure 7:
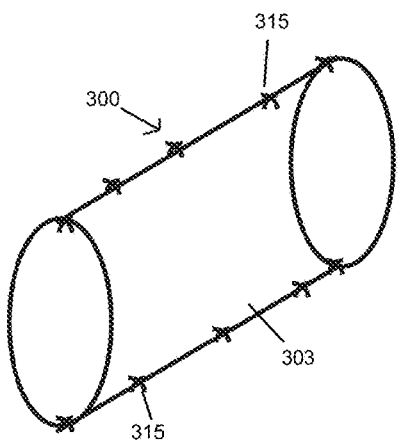
FIG. 7 is a perspective view illustrating an endovascular repair graft manufactured according to an embodiment of the present disclosure.

As illustrated in FIG. 7, the repair graft 300 significantly reduces the amount of hand stitching required to secure graft material 303 to wires forming a lumen, resulting in improved manufacturing costs, efficiency, and design. By providing a sleeve or a pocket at the ends of the graft material 303, the rings forming the wire lumen may be "sleeved" into the graft material 303, thereby eliminating, or at least minimizing the need for utilizing labor-intensive processes, such as hand-stitching, for securing the rings to the graft material 303. Moreover, this improved design for securing the graft material 303 to the wire rings may decrease the need for a large number of hand stitched suture knots along the length of the spine.

Figure 8:
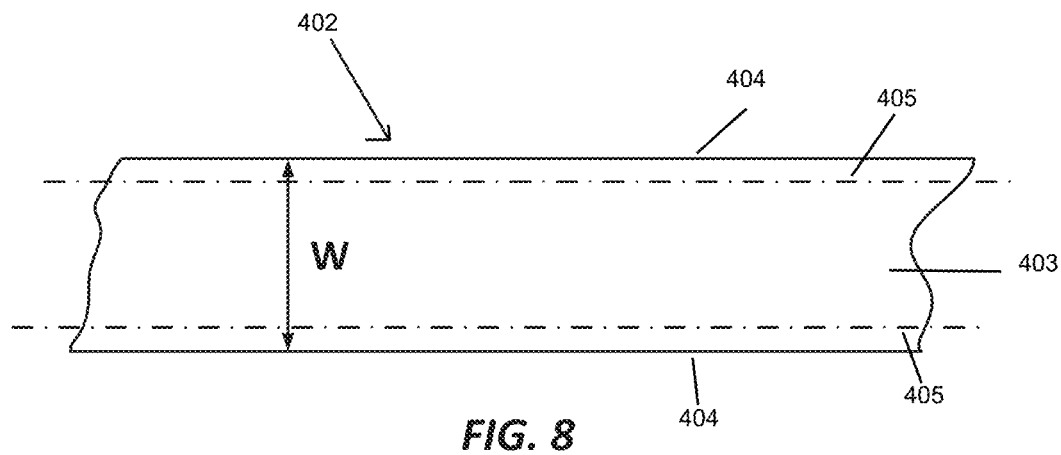
FIG. 8 is a top view illustrating a ribbon of graft material having a width W for manufacturing an endovascular repair graft according to additional embodiments of the present disclosure.
Figure 9:
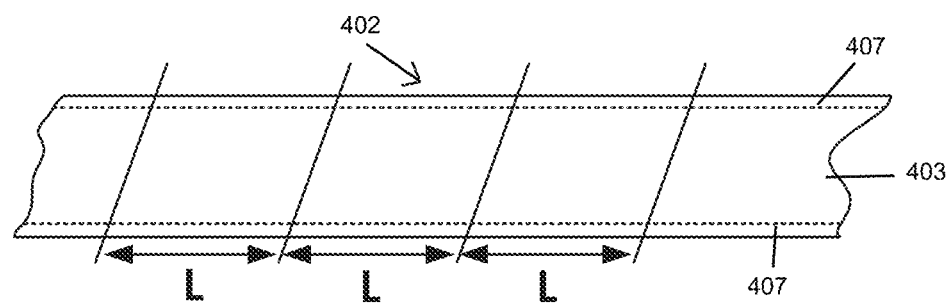
FIG. 9 is a top view illustrating the ribbon of graft material of FIG. 8, cut at intervals having a length L.

FIGS. 8-9 are top views illustrating a ribbon 402 of graft material 403 for manufacturing endovascular repair grafts according to additional embodiments of the present disclosure. Unlike the tubular graft material 302 of the prior embodiment, the embodiments of FIGS. 10-12 described herein are manufactured using a premade ribbon 402 of graft material 403, which is formed into a tubular shape during manufacture of the repair graft. The graft material 403 may be comprised of any suitable graft material known in the art, including, for example, a polyester, such as Dacron.

As shown in FIG. 8, the ribbon 402 of graft material 403 may have a width W, selected according to a particular patient's anatomy. That is, the width W may be calculated by determining the desired length of the endovascular repair graft, and adding additional material for forming sleeves or pockets at the ends of the endovascular repair graft. For example, to manufacture an endovascular repair graft having a length of 20 mm, a width W of 30 mm may be selected to provide 10 mm additional material for forming sleeves or pockets at the ends of the endovascular repair graft.

The sleeves or pockets at the ends of the endovascular repair graft are formed by folding the side edges 404 of the ribbon 402 toward sewing lines 405, indicated in FIG. 8 by dashed lines. The sewing lines 405 may be positioned relative to the side edges 404 of the ribbon 402 to accommodate the size and shape of the small loop and larger ring of the first wire and the second wire formed into a "tad-pole shape", or any other generally closed shape, as discussed above. For example, each sewing line 405 may be set 5 mm from the side edge 404.

Once folded, the side edges 404 of the ribbon 402 may be secured to the ribbon 402 along seams 407, such that 2.5 mm width sleeves or pockets are formed. The seams 407 may be formed by any suitable non-labor intensive means, including for example, suture string sewn with a conventional sewing machine, heat staking, or adhesives. The seams 407 may be formed along the entire length of ribbon 402. For example, the seams 407 may be pre-manufactured such that the ribbon 402 with seams 407 may be cut, as needed.

As shown in FIG. 9, the ribbon 402 may then be cut at intervals having a length L, selected according to a particular patient's anatomy. That is, the length L may be calculated by determining the circumference of the aortic vessel needing repair, and adding additional material for forming sleeves or pockets extending along the length of the endovascular repair graft, as described herein. For example, for an endovascular repair graft having one sleeve or pocket extending along the length of the endovascular repair graft (as in the embodiment of FIG. 11 described below), 5 mm of additional material may be added to the determined circumference of the aortic vessel needing repair, resulting in a 2.5 mm sleeve or pocket. For an endovascular repair graft having two sleeves or pockets extending along the length of the endovascular repair graft (as in the embodiment of FIG. 12 described below), 10 mm of additional material may be added, resulting in two 2.5 mm sleeves or pockets.

FIGS. 10A-G illustrate the manufacture of an endovascular repair graft 500 according to an embodiment of the present disclosure, using the ribbon 402 shown and described with reference to FIGS. 8-9. As described below, the endovascular repair graft 500 is configured as a repair graft having sleeves or pockets 521 formed at the ends of the repair graft 500 for receiving nitinol rings, without a sleeve or pocket extending along the length of the endovascular repair graft for receiving a wire spine.

Figure 10A:
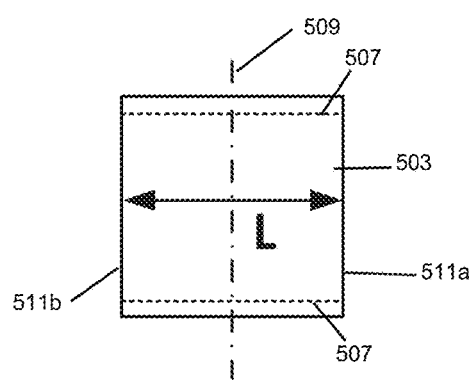
FIGS. 10A-G are top, side, and perspective views illustrating the manufacture of an endovascular repair graft according to an embodiment of the present disclosure.
Figure 10B:
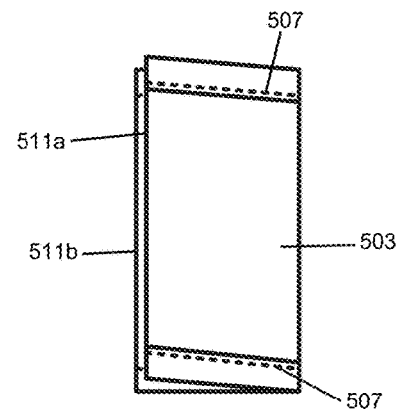

FIG. 10A is a top view of a length L of graft material 503 cut from the ribbon 402 having seams 507. A fold line 509 is illustrated in FIG. 10A by a dashed line. As shown in the top view of FIG. 10B, the length L of graft material 503 is folded in half along the fold line 509, such that ends 511a and 511b of the graft material 503 are aligned with one another.

Figures 10C, 10D, 10E:
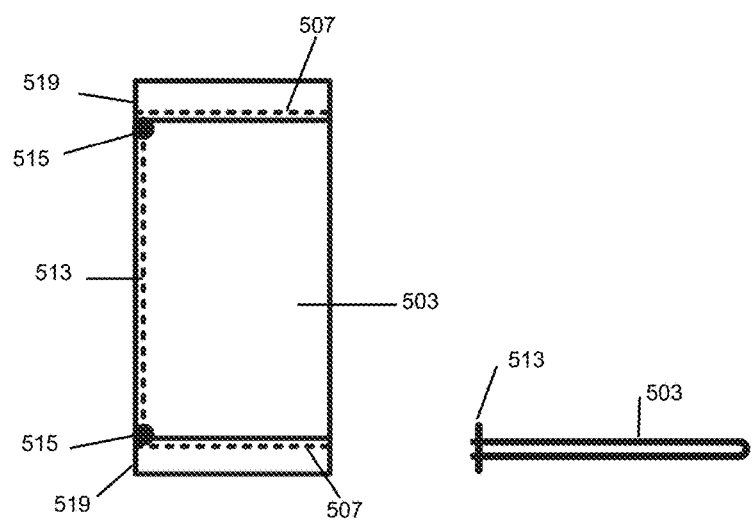

Once folded, a longitudinal seam 513 may be formed along the length of the graft material 503, between the seams 507, as shown in the top view of FIG. 10C. Again, the seam 511 may be formed by any suitable non-labor intensive means, including for example, suture string sewn with a conventional sewing machine, heat staking, or adhesives. The seam 511 may terminate at a location adjacent to the seams 507 via a knot or tie-off 515 to prevent the seam 513 from coming undone.

Once the seam 513 is complete, a slit 519 remains at the ends 511a and 511b of the graft material 503, adjacent the seam 513, and in the sleeves or pockets 521 formed by seams 507. As illustrated in the side view of FIG. 10D, the graft material 503 with seam 513 forms a generally tubular shape that may be stented open via wires to create a circular lumen therethrough (best seen in FIG. 10F).

Next, as illustrated in the top view of FIG. 10E, the graft material 503 may be trimmed along cut lines 517. The graft material 503 may be trimmed by any suitable means, including for example, a thermal knife, a soldering iron, or a blade. The cut lines 517 are positioned so as to create or widen slits 519 in the sleeves or pockets 521 formed by seams 507. With the slits 519 created, the small loops 107a, 107b and the larger rings 109a, 109b of the first wire 105a and the second wire 105b formed into a "tad-pole shape", or any other generally closed shape, as discussed above, may be "sleeved" or advanced via the slits 519 through the sleeves 521 formed in the graft material 503. Alternatively, the wire ring 119 of FIGS. 2B-C may be used.

Figure 10F:
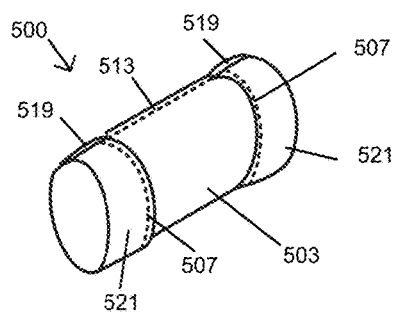
Figure 10G:
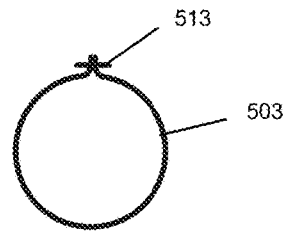

FIG. 10F illustrates an endovascular repair graft 500 stented open by the first wire 105a and the second wire 105b formed into a "tad-pole shape", as described above. FIG. 10G is a cross-sectional side view illustrating the stented open graft material 503. Once the small loops 107a, 107b and the larger rings 109a, 109b are fully sleeved into the sleeves 521, the spines 111a, 111b may be secured to the graft 503, for example, with hand stitched suture knots. Alternatively, the spine 115 of FIG. 2A may be used. A hand stitched suture knot may also be used to secure the first small loops 107a, 107b and the second small loop 113a, 113b to the graft material 503. The sleeves 521 effectively secure the graft material 503 to the larger rings 109a, 109b, such that no hand-stitched suture knots are required to secure the larger rings 109a, 109b to the graft material 503. However, it should be appreciated that one or more hand stitched suture knots may be used to further secure the larger rings 109a, 109b to the graft material 503.

As with the prior embodiment, the repair graft 500 significantly reduces the amount of hand stitching required to secure graft material 503 to wires forming a lumen, resulting in improved manufacturing costs, efficiency, and design. By providing a sleeve or a pocket 521 at the ends of the graft material 503, the rings forming the wire lumen may be "sleeved" into the graft material 503, thereby eliminating, or at least minimizing the need for utilizing labor-intensive processes, such as hand-stitching, for securing the rings to the graft material 503. Moreover, this improved design for securing the graft to the wire rings may decrease the need for a large number of hand stitched suture knots along the length of the spine.

FIGS. 11A-G illustrate the manufacture of an endovascular repair graft 600 according to an embodiment of the present disclosure, using the ribbon 402 shown and described with reference to FIGS. 8-9. As described below, the endovascular repair graft 600 is configured as a graft having sleeves or pockets 621 formed at the ends of the repair graft 600 for receiving nitinol rings, and a single sleeve or pocket 623 extending along the length of the repair graft 600 for receiving a wire spine.

Figure 11A:
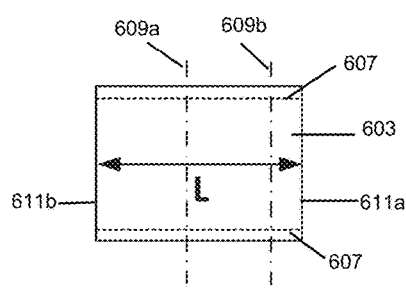
FIGS. 11A-G are top, side, and perspective views illustrating the manufacture of an endovascular repair graft according to an embodiment of the present disclosure; and, FIGS. 12A-G are top, side, and perspective views illustrating the manufacture of an endovascular repair graft according to an embodiment of the present disclosure.
Figure 11B:
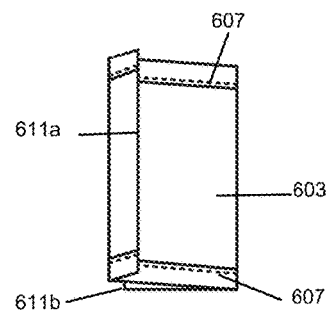

FIG. 11A is a top view of a length L of graft material 603 cut from the ribbon 402 having seams 607. Two fold lines 609a and 609b are illustrated in FIG. 11A by dashed lines. As shown in the top view of FIG. 11B, the length L of graft material 603 is folded about fold line 609a, such that a first end 611a of the graft material 603 extends beyond a second end 611b of the graft material 603. The graft material 603 is then folded back along fold line 609b, such that the first end 611a and the second end 611b are slightly overlapping.

Figure 11C:
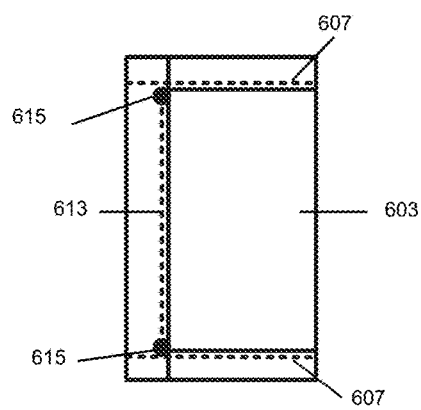

Once folded, a longitudinal seam 613 may be formed along the length of the graft material 603, between the seams 607, as shown in the top view of FIG. 11C. The seam 613 may be formed by any suitable non-labor intensive means, including for example, suture string sewn with a conventional sewing machine, heat staking, or adhesives. The seam 613 may terminate at a location adjacent to the seams 607 via a knot or tie-off 615 to prevent the seam 613 from coming undone.

Figure 11D:
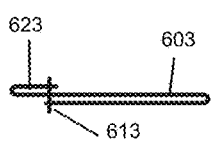
Figure 11E:
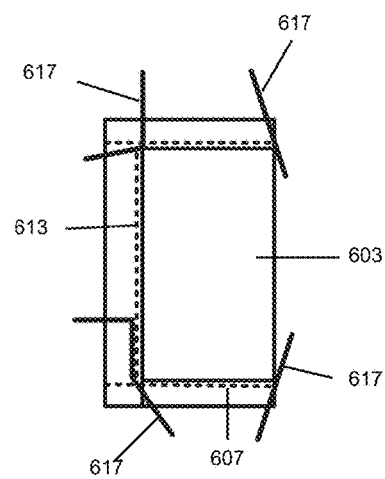
Figure 11F:
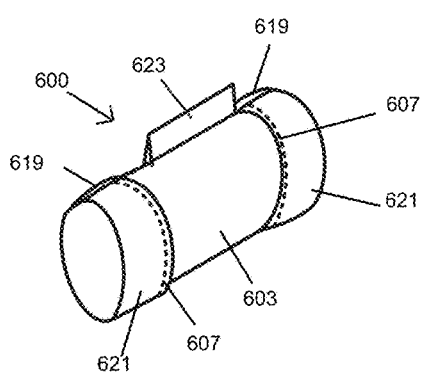

As illustrated in the side view of FIG. 11D, once the seam 613 is complete, the graft material 603 with seam 613 creates a generally tubular shape that may be stented open via wires to create a circular lumen therethrough (best seen in FIG. 11F). The seam 613 also forms a longitudinal sleeve or pocket 623 extending along the length of the endovascular repair graft 600 for receiving a wire spine.

Next, as illustrated in the top view of FIG. 11E, the graft material 603 may be trimmed along cut lines 617. The graft material 603 may be trimmed by any suitable means, including for example, a thermal knife, a soldering iron, or a blade. The cut lines 617 are positioned so as to create slits 619 in the sleeves or pockets 621 formed by seams 607, and also to remove a portion of the pocket or sleeve 623 extending along the length of the endovascular repair graft 600. With the slits 619 created, the small loop 107a and the larger ring 109a of the first wire 105a formed into a "tad-pole shape", or any other generally closed shape, as discussed above, may be "sleeved" or advanced via the slits 619 through the sleeves 621 formed in the graft material 603. Alternatively, the wire ring 119 of FIGS. 2B-C may be used.

Figure 11G:
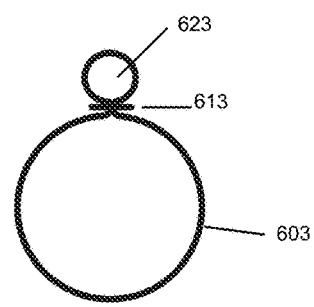

FIG. 11F illustrates an endovascular repair graft 600 stented open by a first wire 105a and a second wire 105b formed into a "tad-pole shape", as described above. FIG. 11G is a cross-sectional side view illustrating the stented open graft material 503. Once the small loop 107a and the larger ring 109a of the first wire 105a are fully sleeved into one of the sleeves 621, the spine 111a may be inserted through the sleeve 623 extending along the length of the repair graft 600. Alternatively, the spine 115 of FIG. 2A may be used. Hand stitched suture knots may then be used to secure the first small loop 107a and the second small loop 113a to the graft material 603. The sleeves 621 and 623 effectively secure the graft material 603 to the larger ring 109a and the spine 111a, such that no hand-stitched suture knots are required to secure the larger ring 109a and the spine 111a to the graft material 603. However, it should be appreciated that one or more hand stitched suture knots may be used to further secure the larger ring 109a to the graft material 603. Likewise, one or more hand stitched suture knots may be used to further secure the spine 111a to the graft material 603. The second wire 105b may be sleeved into the other sleeve 621 and secured to the graft material 603 with suture knots, as described above with reference to the endovascular repair graft 500.

As with prior embodiments, the repair graft 600 significantly reduces the amount of hand stitching required to secure graft material 603 to wires forming a lumen, resulting in improved manufacturing costs, efficiency, and design. By providing a sleeve or a pocket 621 at the ends of the graft material 603, and by providing a sleeve or pocket 623 extending along the length of the graft material 603, the rings and spine forming the wire lumen may be "sleeved" into the graft material 603, thereby eliminating, or at least minimizing the need for utilizing labor-intensive processes, such as hand-stitching, for securing the rings and spine to the graft material 603. Moreover, this improved design for securing the graft to the wire rings may decrease the need for a large number of hand stitched suture knots along the length of the spine.

FIGS. 12A-G illustrate the manufacture of an endovascular repair graft 700 according to an embodiment of the present disclosure, using the ribbon 402 shown and described with reference to FIGS. 8-9. As described below, the endovascular repair graft 700 is configured as a graft having sleeves or pockets 721 formed at the ends of the repair graft 700 for receiving nitinol rings, and with two sleeves or pockets 723a and 723b extending along the length of the endovascular repair graft 700 for receiving wire spines.

Figure 12A:
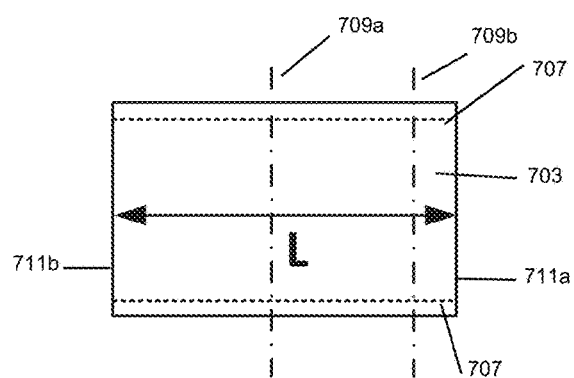
Figure 12B:
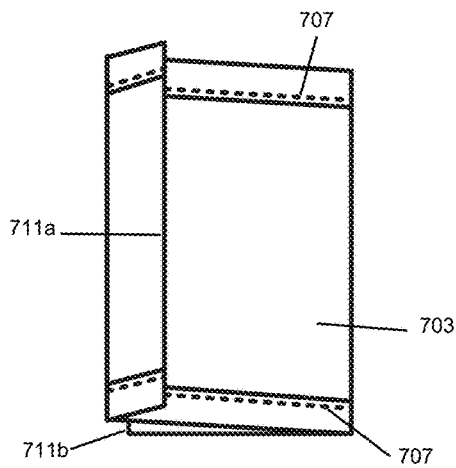

FIG. 12A is a top view of a length L of graft material 703 cut from the ribbon 702 having seams 707. Two fold lines 709a and 709b are illustrated in FIG. 12A by dashed lines. As shown in the top view of FIG. 12B, the length L of graft material 703 is folded about fold line 709a, such that a first end 711a of the graft material 703 extends beyond a second end 711b of the graft material 703. The graft material 703 is then folded back along fold line 709b, such that the first end 711a and the second end 711b are slightly overlapping.

Figure 12C:
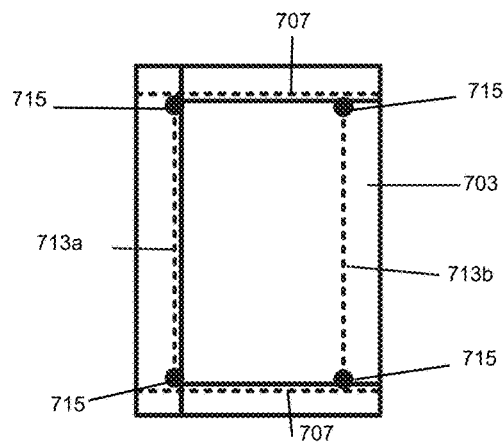

Once folded, a first longitudinal seam 713a and a second longitudinal seam 713b may be formed along the length of the graft material 703, between the seams 707, as shown in the top view of FIG. 12C. The seams 713 may be formed by any suitable non-labor intensive means, including for example, suture string sewn with a conventional sewing machine, heat staking, or adhesives. The seams 713 may terminate at a location adjacent to the seams 707 via a knot or tie-off 715 to prevent the seams 713a and 713b from coming undone.

Figure 12F:
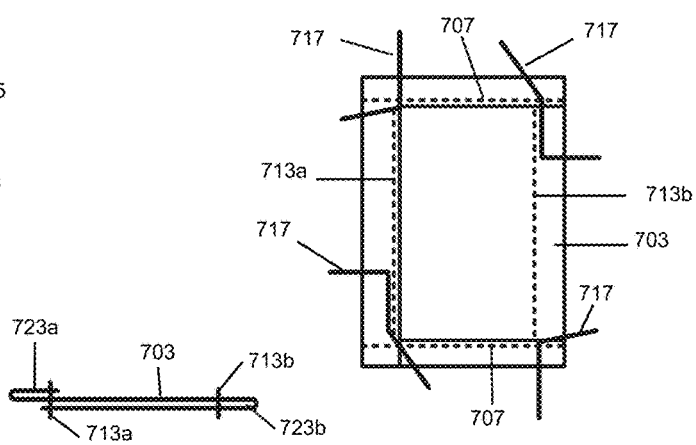
Figure 12F:
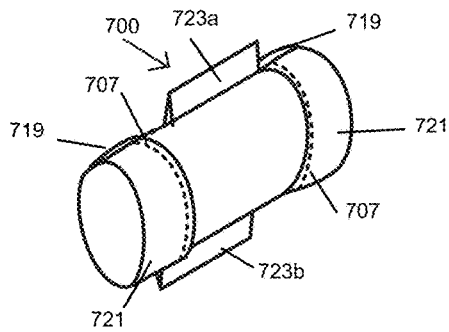

As illustrated in the side view of FIG. 12D, the graft material 703 with seams 713a and 713b creates a generally tubular shape that may be stented open via wires to create a circular lumen therethrough (best seen in FIG. 12F). The seams 713a and 713b also form longitudinal sleeves or pockets 723a and 723b extending along the length of the endovascular repair graft 700 for receiving wire spines.

Next, as illustrated in the top view of FIG. 12E, the graft material 703 may be trimmed along cut lines 717. The graft material 703 may be trimmed by any suitable means, including for example, a thermal knife, a soldering iron, or a blade. The cut lines 717 are positioned so as to create slits 719 in the sleeves or pockets 721 formed by seams 707, and also to remove a portion of the pockets or sleeves 723a and 723b extending along the length of the endovascular repair graft 700. With the slits 719 created, the small loops 107a and 107b and the larger rings 109a and 109b of the first wire 105a and the second wire 105b formed into a "tad-pole shape", or any other generally closed shape, as discussed above, may be "sleeved" or advanced via the slits 719 through the sleeves 721 formed in the graft material 703. Alternatively, the wire ring 119 of FIGS. 2B-C may be used.

Figure 12G:
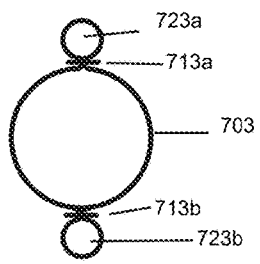

FIG. 12F illustrates an endovascular repair graft 700 stented open by a first wire 105a and the second wire 105b formed into a "tad-pole shape", as described above. FIG. 12G is a cross-sectional side view illustrating the stented open graft material 703. Once the small loops 107a and 107b and the larger rings 109a and 109b of the first wire 105a and the second wire 105b are fully sleeved into the sleeves 721, the spines 111a and 111b may be inserted through the sleeves 723a and 723b extending along the length of the repair graft 700. Alternatively, the spine 115 of FIG. 2A may be used. Hand stitched suture knots may then be used to secure the first small loops 107a and 107b and the second small loops 113a and 113b to the graft material 703. The sleeves 721, 723*a* and 723*b* effectively secure the graft material 703 to the larger rings 109*a* and 109*b*, and the spines 111*a* and 111*b*, such that no hand-stitched suture knots are required to secure the larger rings 109*a* and 109*b* or the spines 111*a* and 111*b* to the graft material 703. However, it should be appreciated that one or more hand stitched suture knots may be used to further secure the larger rings 109*a* and 109*b* to the graft material 703. Likewise, one or more hand stitched suture knots may be used to further secure the spines 111*a* and 111*b* to the graft material 703.

As with prior embodiments, the repair graft 700 significantly reduces the amount of hand stitching required to secure graft material 703 to wires forming a lumen, resulting in improved manufacturing costs, efficiency, and design. By providing a sleeve or a pocket 721 at the ends of the graft material 703, and by providing two sleeves or pockets 723 extending along the length of the graft material 703, the rings and spines forming the wire lumen may be "sleeved" into the graft material 703, thereby eliminating, or at least minimizing the need for utilizing labor-intensive processes, such as hand-stitching, for securing the rings and spines to the graft material 703. Moreover, this improved design for securing the graft to the wire rings may decrease a need for a large number of hand stitched suture knots along the length of the spines.

The repair grafts 800A-K of FIGS. 1A-K will not be described in detail. FIGS. 1A-K are side views illustrating various endovascular repair grafts 800A-K manufactured according to conventional weaving, knitting, or braiding processes, or a combination thereof. The repair grafts 800A-K of FIGS. 1A-K may be manufactured using conventional weaving, knitting, or braiding machines, such as for example, a shuttle loom in the case of weaving.

Figure 1A:
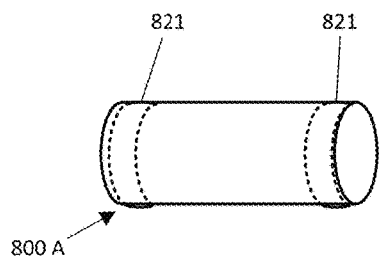
FIGS. 1A-K are side views illustrating various endovascular repair grafts according to an embodiment of the present disclosure manufactured according to conventional weaving, knitting, or braiding processes.
Figure 1B:
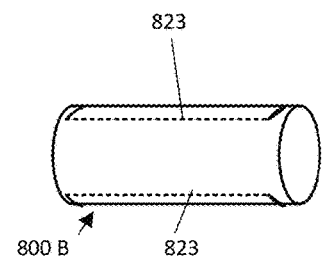
Figure 1C:
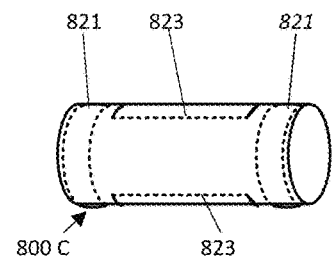
Figure 1D:
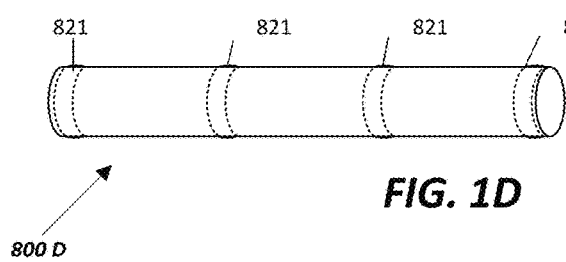
Figure 1E:
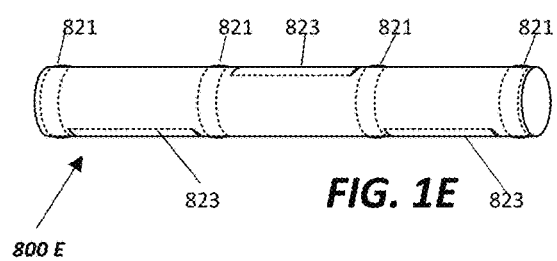
Figure 1F:
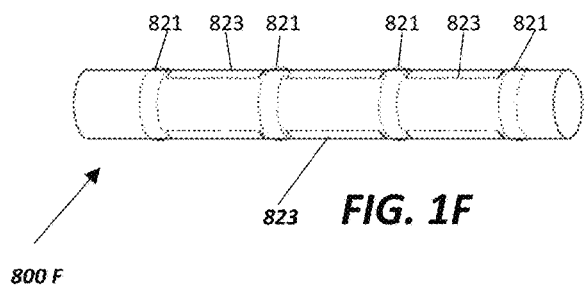
Figure 1G:
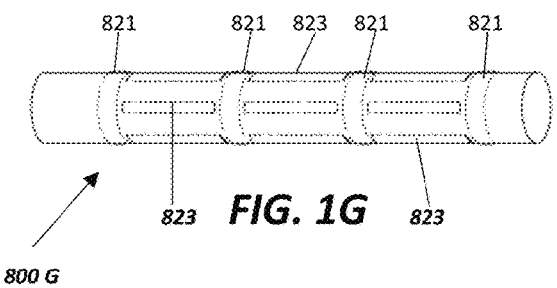
Figure 1H:
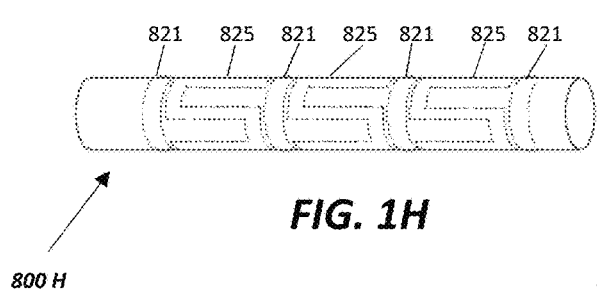
Figure 1I:
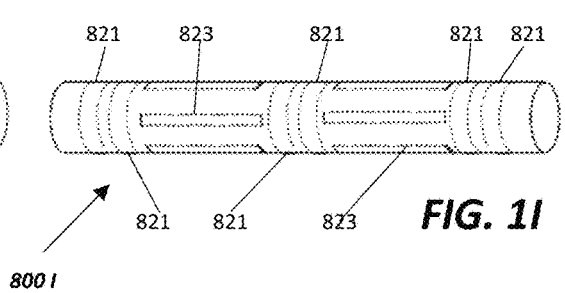
Figure 1J:
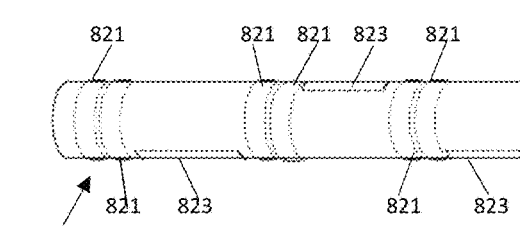
Figure 1K:
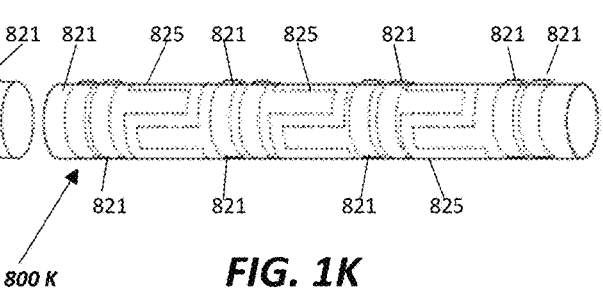

Similar to the previously described embodiments, the repair grafts 800A-K may include a plurality of circumferential sleeves or pockets 821, longitudinal sleeves or pockets 823, and sleeves or pockets 825 having an orientation or pattern extending in both a circumferential and a longitudinal direction (e.g., as shown in FIGS. 1H and 1K). The sleeves 821, 823, and 825 of repair grafts 800A-K may be integrally formed with a tubular body of the repair graft during the process of making the tubular body (i.e., by weaving, knitting, or braiding), such that the graft material is not folded onto itself and secured with a seam, as described in the prior embodiments. In other words, the sleeves 821, 823, and 825 are integrally formed with the same thread or threads as the tubular body during the weaving, knitting, or braiding process.

In the case of a woven endovascular repair graft, for example, the fabric structure (i.e., weave design) of the sleeves 821, 823, and 825 may be the same as the tubular body of the endovascular repair graft, or it may contain a different fabric structure or density (e.g., material, yarn/thread construction, warp/weft density, etc.). The same methodology and options may also be applied to knitted or braided endovascular repair grafts. Selection of different weave designs and fabric structures or densities may advantageously reduce the profile of the repair graft.

The circumferential sleeve or pockets 821 may be located at one end, both ends, or at multiple positions along the length of the repair graft, as shown in the various repair grafts 800A-K. For example, the circumferential sleeve or pockets 821 may be positioned at the end of the repair graft (e.g., as seen in FIGS. 1A and 1C-1E), or a short distance from the end of the repair graft (e.g., as seen in FIGS. 1F-1K). Additionally, the circumferential sleeve or pockets 821 may be positioned and spaced individually along the length of the repair graft (e.g., as seen in FIGS. 1A and 1C-1H), or two or more circumferential sleeves or pockets 821 may be positioned and spaced next to one another along the length of the repair graft (e.g., as seen in FIGS. 1I-1K).

The longitudinal sleeves or pockets 823 may be located at one or multiple locations about the circumference of the repair graft, as shown in FIGS. 1B-1C, 1E-1G, and 1I-1J. The longitudinal sleeves or pockets 823 may extend the entire length of the repair graft, or only a portion of the length of the repair graft, such as for example, when circumferential sleeves or pockets 821 are periodically spaced along the length of the repair graft.

The orientation of the circumferential sleeve or pockets 821 and the longitudinal sleeves or pockets 823 are not limited respectively to a discrete circle or a straight line; rather, they could have an orientation or pattern extending in both a circumferential and a longitudinal direction, for example, as shown with sleeves or pockets 825 in FIGS. 1H and 1K. Such sleeves or pockets 825 could take other shapes or orientations, including for example, a helix with one or multiple turns, or some other combination diagonal portions, circumferential portions, and/or longitudinal portions.

The sleeves 821, 823, and 825 may further include openings (similar to the previously described slits) at one or more locations to receive a wire ring (for example, as described above with regard to the ring 109*a*, 109*b*, 119) or a wire spine (for example, as described above with regard to the spine 111*a*, 111*b*, 115). The openings may be formed during the weaving, knitting, or braiding process, or as a post processing step, for example with a thermal knife, a soldering iron, or a blade. After insertion of a wire ring or a wire spine, these openings may be left open, or they may be closed by any suitable means, including sewing or with suture knots.

Depending on the shape and orientation of the sleeves, a wire 105*a*, 105*b* formed into a "tad-pole" shape, or individual wire rings 119 and wire spines 115 may be inserted or advanced into the sleeves. For example, with the configuration of circumferential sleeves 821 and longitudinal sleeves 823 shown in FIG. 1C, a wire 105*a*, 105*b* formed into a "tad-pole" shape may be used. Alternatively, in FIG. 1C, and in the alternative configurations of FIGS. 1A-1K, individual wire rings 119 and wire spines 115 may be respectively inserted into the circumferential sleeves 821 and the longitudinal sleeves 823. Wires of other shapes or patterns (with or without small loops encircling the ends of the wire) may be formed for use in a sleeve or pocket 825 having an orientation or pattern extending in both a circumferential and a longitudinal direction (for example, as shown in FIGS. 1H and 1K).

As with the previously discussed embodiments, these wire rings and spines may be may be "sleeved" into the sleeves 821, 823, 825 through one or more openings, thereby eliminating, or at least minimizing the need for utilizing labor-intensive processes, such as hand-stitching, for securing the rings and spines to the material of the repair grafts 800A-K. For example, hand stitching of such rings or spines may be limited to a single hand stich to secure a small loop (e.g., 107*a*, 170*b*, 121*a*, 121*b*) of a ring, or a small loop (e.g., 111*a*, 111*b*, 117*a*, 117*b*) of a spine. In some cases, particularly where the opening to the sleeve or pocket is closed, the wire rings or spines may be fully enclosed and secured within the sleeves 821, 823, 825, such that no hand stitching is required.

The invention claimed is:
1. An endoluminal graft comprising:
a tubular graft having a lumen;

a first closed sleeve separate from and adjacent to the lumen, the first closed sleeve positioned at a first end of the endoluminal graft and comprising an interior void extending along a circumference of the first end about a periphery of the lumen;

a second closed sleeve separate from and adjacent to the lumen, the second closed sleeve positioned at a second end of the endoluminal graft opposite the first end, the second closed sleeve comprising an interior void extending along a circumference of the second end about a periphery of the lumen;

a first wire having a first length formed into a generally closed shape and a second length formed into a spine, wherein the first length of the first wire formed into the generally closed shape is at least partially enclosed within the first closed sleeve, and the second length of the first wire formed into the spine extends toward the second end of the endoluminal graft; and, a second wire having a first length formed into a generally closed shape and a second length formed into a spine, wherein the first length of the second wire formed into the generally closed shape is at least partially enclosed within the second closed sleeve, and the second length of the second wire formed into the spine extends toward the first end of the endoluminal graft;

wherein the tubular graft, the first closed sleeve, and the second closed sleeve comprise a single piece of graft material;

wherein the second length of the first wire comprises a first loop formed at the second end of the endoluminal graft, and the second length of the second wire comprises a second loop formed at the first end of the endoluminal graft; and, wherein the first loop of the first wire is anchored to the second wire.

2. The endoluminal graft of claim 1, wherein the first closed sleeve and the second closed sleeve are integral with the tubular graft and characterized by the absence of any circumferential seam.

3. The endoluminal graft of claim 1, wherein the single piece of graft material is a textile.

4. The endoluminal graft of claim 1, wherein the first loop of the first wire is anchored to the second wire via a suture.

5. The endoluminal graft of claim 1, wherein the second loop of the second wire is anchored to the first wire.

6. The endoluminal graft of claim 1, wherein the first wire is anchored to the second wire at the locations of the first loop and the second loop.

7. The endoluminal graft of claim 1, wherein the second length of the first wire and the second length of the second wire are positioned opposite one another along a length of the endoluminal graft.

8. The endoluminal graft of claim 1, wherein the second length of the first wire formed into the spine is at least partially enclosed within a closed longitudinal sleeve adjacent to the lumen and extending toward the second end of the endoluminal graft.

9. The endoluminal graft of claim 1, wherein the second length of the second wire formed into the spine is at least partially enclosed within a closed longitudinal sleeve adjacent to the lumen and extending toward the first end of the endoluminal graft.

10. An endoluminal graft comprising:
a tubular graft having a lumen;
a first closed sleeve separate from and adjacent to the lumen, the first closed sleeve positioned at a first end of the endoluminal graft and comprising an interior void extending along a circumference of the first end about a periphery of the lumen;

a second closed sleeve separate from and adjacent to the lumen, the second closed sleeve positioned at a second end of the endoluminal graft opposite the first end, the second closed sleeve comprising an interior void extending along a circumference of the second end about a periphery of the lumen;

a first wire having a first length formed into a generally closed shape and a second length formed into a spine and a first loop, wherein the first length of the first wire formed into the generally closed shape is at least partially enclosed within the first closed sleeve, and the second length of the first wire formed into the spine extends to the second end of the endoluminal graft, with the first loop being located at the second end; and, a second wire having a first length formed into a generally closed shape and a second length formed into a spine and a second loop, wherein the first length of the second wire formed into the generally closed shape is at least partially enclosed within the second closed sleeve, and the second length of the second wire formed into the spine extends toward the first end of the endoluminal graft, with the second loop being located at the first end;

wherein the first wire is anchored to the second wire at the location of the first loop and the second loop; and, wherein the tubular graft, the first closed sleeve, and the second closed sleeve comprise a single piece of graft material.

11. The endoluminal graft of claim 10, wherein the second length of the first wire and the second length of the second wire are positioned opposite one another along a length of the endoluminal graft.

12. The endoluminal graft of claim 10, wherein the single piece of graft material is a textile.

13. An endoluminal graft comprising:
a tubular graft having a lumen;
a first closed sleeve separate from and adjacent to the lumen, the first closed sleeve positioned at a first end of the endoluminal graft and comprising an interior void extending along a circumference of the first end about a periphery of the lumen;

a second closed sleeve separate from and adjacent to the lumen, the second closed sleeve positioned at a second end of the endoluminal graft opposite the first end, the second closed sleeve comprising an interior void extending along a circumference of the second end about a periphery of the lumen;

a first wire having a first length formed into a generally closed shape and a second length formed into a spine, wherein the first length of the first wire formed into the generally closed shape is at least partially enclosed within the first closed sleeve, and the second length of the first wire formed into the spine extends toward the second end of the endoluminal graft; and, a second wire having a first length formed into a generally closed shape and a second length formed into a spine, wherein the first length of the second wire formed into the generally closed shape is at least partially enclosed within the second closed sleeve, and the second length of the second wire formed into the spine extends toward the first end of the endoluminal graft;

wherein the tubular graft, the first closed sleeve, and the second closed sleeve comprise a single piece of graft material; and, wherein the second length of the first wire formed into the spine is at least partially enclosed within a closed longitudinal sleeve adjacent to the lumen and extending toward the second end of the endoluminal graft.

14. The endoluminal graft of claim 13, wherein the first closed sleeve and the second closed sleeve are integral with the tubular graft and characterized by the absence of any circumferential seam.

15. The endoluminal graft of claim 13, wherein the single piece of graft material is a textile.

16. The endoluminal graft of claim 13, wherein the second length of the first wire comprises a first loop formed at the second end of the endoluminal graft, and the second length of the second wire comprises a second loop formed at the first end of the endoluminal graft.

17. The endoluminal graft of claim 16, wherein the first loop of the first wire is anchored to the second wire.

18. The endoluminal graft of claim 16, wherein the second loop of the second wire is anchored to the first wire.

19. The endoluminal graft of claim 13, wherein the second length of the first wire and the second length of the second wire are positioned opposite one another along a length of the endoluminal graft.

20. The endoluminal graft of claim 13, wherein the second length of the second wire formed into the spine is at least partially enclosed within a closed longitudinal sleeve adjacent to the lumen and extending toward the first end of the endoluminal graft.

\* \* \* \* \*